United States Patent [19]
Hoehn et al.

[11] 3,966,746
[45] June 29, 1976

[54] AMINO DERIVATIVES OF PYRAZOLOPYRIDINE CARBOXAMIDES

[75] Inventors: Hans Hoehn, Tegernheim; Theodor Denzel, Nurnberg, both of Germany

[73] Assignee: E. R. Squibb & Sons, Inc., Princeton, N.J.

[22] Filed: June 4, 1975

[21] Appl. No.: 583,373

Related U.S. Application Data

[60] Continuation of Ser. No. 489,636, July 18, 1974, abandoned, which is a division of Ser. No. 306,967, Nov. 15, 1972, Pat. No. 3,840,456.

[52] U.S. Cl.................... 260/293.6; 260/268 BC; 260/294.8 C; 260/295.5 B
[51] Int. Cl.².................................. C07D 471/04
[58] Field of Search.... 260/268 BC, 293.6, 294.8 C, 260/295.5 B

[56] References Cited
OTHER PUBLICATIONS
Hoehn, et al., "Chem. Abstracts," vol. 81, (1974) No. 37544d.

*Primary Examiner*—Henry R. Jiles
*Assistant Examiner*—R. W. Ramsuer
*Attorney, Agent, or Firm*—Lawrence S. Levinson; Merle J. Smith; Donald J. Barrack

[57] ABSTRACT

4-Amino derivatives of pyrazolo[3,4-b]pyridine-5-carboxamides having the formula

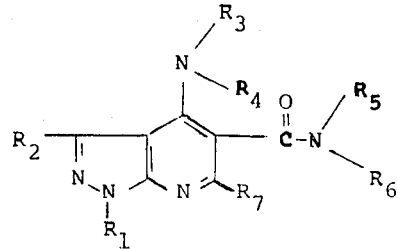

are disclosed. The novel compounds are useful as ataractic, analgesic, and hypotensive agents.

8 Claims, No Drawings

AMINO DERIVATIVES OF PYRAZOLOPYRIDINE CARBOXAMIDES

This is a continuation of application Ser. No. 489,636, filed July 18, 1974, now abandoned, which is a division of application Ser. No. 306,967, filed Nov. 15, 1972, now U.S. Pat. No. 3,840,456.

SUMMARY OF THE INVENTION

This invention relates to new 4-amino derivatives of pyrazolo[3,4-b]pyridine-5-carboxamides and salts of these compounds. These new compounds have the formula I 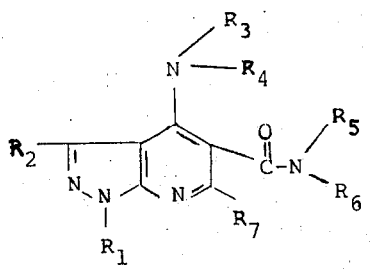

The symbols have the following meaning in formula I and throughout the specification:

$R_1$ is hydrogen, lower alkyl, phenyl, phenyl-lower alkyl, or cycloalkyl.

$R_2$ is hydrogen, lower alkyl, or phenyl.

The basic nitrogen group

is an acyclic amino group wherein $R_3$ and $R_4$ may each be hydrogen, lower alkyl, lower alkenyl, lower alkanoyl, phenyl, substituted phenyl, phenyl-lower alkyl, di-lower alkyl amino-lower alkyl, benzoyl, substituted benzoyl, phenyl-lower alkanoyl, substituted phenyl-lower alkanoyl, alkanesulfonyl, benzenesulfonyl, or substituted benzenesulfonyl.

The basic nitrogen group

may also be heterocyclic containing 3,4,5, or 6 members; an additional hetero atom, e.g. nitrogen, oxygen, or sulfur may be included.

The basic nitrogen group

of the carboxamide moiety is an acyclic amino group wherein $R_5$ and $R_6$ may each be hydrogen, lower alkyl, alkoxy lower alkyl, dialkoxy lower alkyl, or di-lower alkylamino-lower alkyl.

The basic nitrogen group

may also be heterocyclic containing 5,6, or 7 members; an additional hetero atom, e.g. nitrogen, oxygen, or sulfur may be included. The heterocyclic moiety may have one or two simple substituents.

$R_7$ is hydrogen, lower alkyl, or phenyl.

DETAILED DESCRIPTION OF THE INVENTION

The lower alkyl and lower alkenyl groups referred to throughout the specification include straight or branched chain hydrocarbon groups containing 1 to 8 carbon atoms. Examples of the type of group contemplated are methyl, ethyl, propyl, isopropyl, butyl, t-butyl, etc., and corresponding compounds having one double bond.

The lower alkanoyl groups referred to throughout the specification include the acyl radicals of acids having the formula $C_nH_{2n+1}COOH$ wherein n must be 7 or less.

The cycloalkyl groups referred to throughout the specification include the 3 to 7 carbon atom alicyclic groups cyclopropyl, cyclobutyl, cyclopentyl, cyclohexyl, and cycloheptyl. The 5 and 6 membered rings are preferred.

The substituted phenyl, substituted benzoyl and substituted benzenesulfonyl groups referred to throughout the specification may include one or two simple substituents, i.e., lower alkyl, halogen (F, Cl, Br, or I; preferably Cl or Br), trifluoromethyl, amino, or carboxy.

Preferred embodiments of this invention are as follows:

$R_1$ is hydrogen or lower alkyl, most preferably hydrogen or ethyl.

$R_2$ is hydrogen or lower alkyl, most preferably hydrogen or methyl.

$R_3$ is lower alkyl, most preferably butyl.

$R_4$ is hydrogen.

Alternatively $R_3$ and $R_4$, together with the nitrogen to which they are attached, may form a 5 or 6 membered heterocyclic such as pyrrolidino, piperidino, pyrazolyl, pyrimidinyl, pyridazinyl, thiodiazinyl, oxadiazinyl, or thiazolyl; most preferred of the 5 and 6 membered rings are pyrrolidino, piperidino, and piperazino.

$R_5$ is lower alkyl, most preferably ethyl.

$R_6$ is hydrogen or lower alkyl, most preferably hydrogen or ethyl.

Alternatively, $R_5$ and $R_6$, together with the nitrogen to which they are attached, may form a 5 or 6 membered heterocyclic; most preferred of the 5 and 6 membered rings are pyrrolidino and piperidino.

$R_7$ is hydrogen or lower alkyl, most preferably hydrogen or methyl.

The new compounds of formula I may be produced by several methods.

According to one procedure, when $R_1$ is other than hydrogen, a product of formula I may be produced from compounds of the formula II 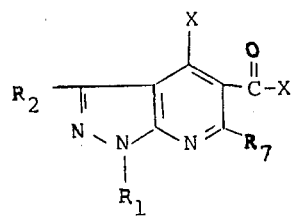

or from compounds of the formula

III 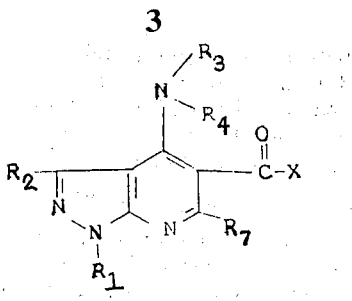

or from compounds of the formula

IV 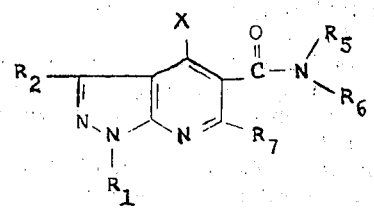

where X is halogen, preferably chlorine or bromine.

The compounds of formula II, III and IV are formed by the following series of reactions. The symbols in the structural formulas have the same meaning as previously described.

A 5-aminopyrazole of the formula

V 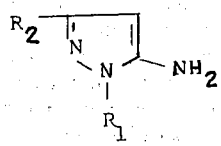

prepared according to the procedure described in Z.f.Chemie 10, 386–388 (1970) is made to react with an alkoxymethylene malonic acid ester of the formula

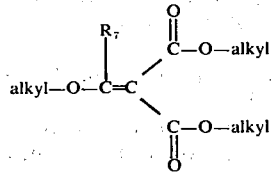 VI by heating at a temperature of about 120°C.
The resulting compound of the formula VII 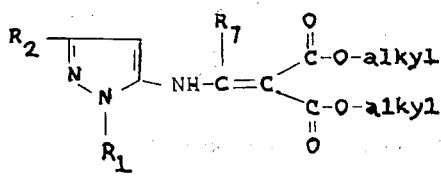

undergoes cyclization in an inert organic solvent such as diphenyl ether at about 230° to 260°C, while distilling off the alcohol formed, producing a compound of the formula VIII 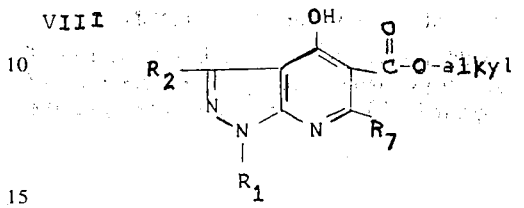

Alternatively, instead of allowing the malonic acid alkyl ester compound of formula VII to undergo cyclization in an inert organic solvent at about 230° to 260° as described above, this product also undergoes cyclization by treatment with phosphorous oxychloride producing the chlorine product of formula IX 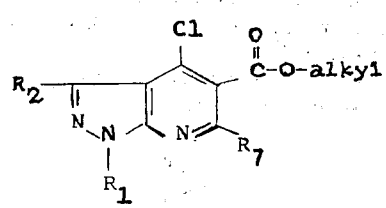

The resulting compounds of formula VIII and IX are saponified by means of sodium- or potassium hydroxide at room temperature providing the corresponding free acids, which in turn are converted by refluxing with thionylchloride to the intermediate of formula II wherein X will be Cl.

The product of formula I is then prepared from a compound of formula II by reaction with the appropriate primary or secondary amine of the formula

 X and the formula

 XI

The reaction for introducing the amino group in position 4 as well as in the carboxamide moiety in position 5 can be effected in either one or two steps. Preferred, however, is the two step reaction because it allows one to prepare derivatives of formula I bearing different amines in the 4 position and as part of the carboxamide moiety. At lower temperatures, e.g., in the range of 0° to 10°C the compound of formula II reacts with the amine of formula X to furnish the intermediate of formula IV which in turn reacts with compounds of formula XI at room temperature providing the amino derivatives of pyrazolo [3,4-b]pyridine-5-carboxamides of formula I.

Alternatively, instead of saponification of the compound of formula IX as described above, this product can be converted to the compound of formula

XII

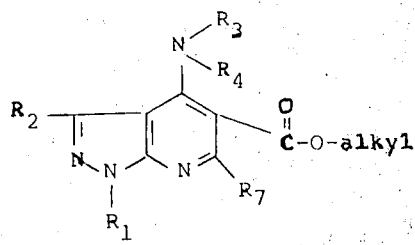

by reaction with the amine of formula XI. The subsequent saponification of the ester of formula XII yields the free acid, which in turn is converted to the acid chloride of formula III. Aminolysis with amines of formula X furnishes the amino derivative of pyrazolo[3,4-b]pyridine-5-carboxamide of formula I. In some cases the direct conversion of the ester to the carboxamide group may be possible and advantageous.

According to a modification of the foregoing procedure, a product of formula I wherein $R_1$ is hydrogen may be produced. By this modification, a 5-aminopyrazole of formula IV wherein $R_1$ is an arylmethyl group or a heteromethyl group is used. This starting material has the formula

XIII

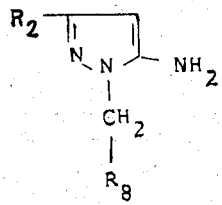

wherein $R_8$ is an aromatic or heterocyclic nucleus-like phenyl, naphthyl, furyl, pyridyl, pyrimidyl, pyrazinyl or the like.

This material is processed as described above through the reaction with the alkoxymethylene malonic acid ester of formula VI, cyclization of the product corresponding to formula VII to obtain a compound of formula VIII, with a hydroxy group in the 4-position, and then alkylating to obtain a compound of formula

XIV

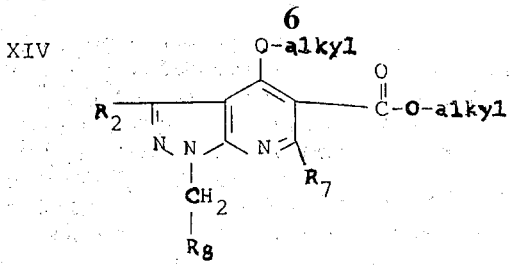

At this point, the compound of formula XIV having in the 1-position the $R_8$—$CH_2$-substituent is oxidized with an oxidizing agent like selenium dioxide in a high boiling solvent like diethyleneglycol dimethylether at about 160° yielding the compound of the formula

XV

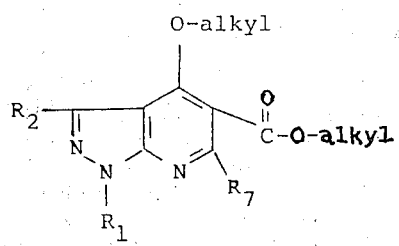

wherein $R_1$ is hydrogen.

The subsequent treatment of the ester of formula XV with the amine of the formula XI provides the compound of the formula XII, which in turn is converted via the acid and acid chloride to the amino derivative of pyrazolo[3,4-b]pyridine-5-carboxamide of formula I. Sometimes it may be advantageous to convert the ester of formula XII directly to compound of formula I by means of reacting the ester group with the amine of formula X at elevated temperatures.

The compounds of formula I form salts which are also part of this invention. The salts include acid-addition salts, particularly the non-toxic, physiologically acceptable ones. The bases of formula I form acid-addition salts by reaction with a variety of inorganic and organic acids. Examples of acid-addition salts are the hydrohalides (especially the hydrochloride), sulfate, nitrate, phosphate, oxalate, tartrate, malate, citrate, acetate, ascorbate, succinate, benzenesulfonate, toluenesulfonate, cyclohexanesulfonate, cyclohexanesulfamate, etc. The acid-addition salts frequently provide a convenient means for isolating the product, e.g., by forming and precipitating the salt in an appropriate menstruum in which the salt is insoluble, then after separation of the salt, neutralizing with a base such as barium hydroxide or sodium hydroxide, to obtain the free base of formula I. Other salts may then be formed from the free base by reaction with an equivalent of acid.

The novel compounds of this invention are central nervous system depressants and are useful as ataractic agents. They find further utility as analgesic and hypotensive agents. They may be used, for example, in mice, cats, rats, dogs and other mammals. For this purpose, a compound or mixture of compounds of formula I, or non-toxic, physiologically acceptable acid addition salts thereof, may be administered orally or parenterally in a conventional dosage form such as tablet, capsule, injectable or the like. A single dose, or preferably 2 to 4 divided doses may be provided on a basis of about 1 to 50 milligrams per kilogram per day, preferably about 2 to 15 mg/kg/day. These may be conventionally formulated in an oral or parenteral dosage form by compounding about 10 to 25 milligrams per unit of dosage with conventional vehicle, excipient, binder, preservative stabilizer, flavor or the like as called for by accepted pharmaceutical practice.

The following examples are specific embodiments of the invention. All temperatures are recorded on the centigrade scale.

EXAMPLE 1

4-Butylamino-1-ethyl-1H-pyrazolo[3,4-b]pyridine-5-(n-butyl)carboxamide, hydrochloride a. [[(1-Ethyl-5-byrazolyl)amino]methylene]malonic acid diethyl ester 245 g of 1-ethyl-5-aminopyrazole (2.2 mol) and 476 g of ethoxymethylene malonic acid diethyl ester (2.2 mol) are heated to 120° (bath temperature) for 2 hours with stirring. The ethanol formed by this reaction is removed by means of a water aspirator. Vacuum distillation (b.p. $_{0.1}$ 154°–160°) yields 520 g (84% of theory) of a quickly crystallizing oil of [[(1-ethyl-5-pyrazolyl)amino]methylene]malonic acid diethyl ester, m.p. 50°–53°. The compound is recrystallized from N-hexane, and has a melting point of 55°–57°.

b. 1-Ethyl-4-hydroxy-1H-pyrazolo[3,4-b]pyridine-5-carboxylic acid ethyl ester 253 g of [[(1-ethyl-5-pyrazolyl)amino]methylene]malonic acid diethyl ester (0.09 mol) is dissolved in 770 g of diphenyl ether. The reaction mixture is heated to 235°–250° (bath temperature) and allowed to react at this temperature for 1 to 2 hours, while the resulting ethanol is continuously distilled off. The remaining alcohol is removed by means of a water aspirator. The diphenyl ether is separated by distillation with a fractionating column in vacuo. The 1-ethyl-4-hydroxy-1H-pyrazolo[3,4-b]pyridinecarboxylic acid ethyl ester is obtained at b.p. $_{0.05}$ 115°–120°, yield 195 g = 92% of theory, m.p. 85°–87°. The compound is recrystallized from ligroin (90° to 100°), and has a melting point of 87°–89°.

c. 1-Ethyl-4-hydroxy-1H-pyrazolo[3,4-b]pyridine-5-carboxylic acid 47 g of 1-ethyl-4-hydroxy-1H-pyrazolo[3,4-b]pyridine-5-carboxylic acid ethyl ester (0.2 mol) are saponified by means of 400 ml of aqueous sodium hydroxide (2.5 N) by refluxing the mixture for 1 ½ hours. After cooling of the filtering solution and diluting with 300 ml of water, it is acidified with glacial acetic acid. The precipitated 1-ehyl-4-hydroxy-1H-pyrazolo[3,4-b]pyridine-5-carboxylic acid is filtered under suction, washed with water and dried at 120°. Yield 37 g (89%), recrystallization from glacial acetic acid, and has a melting point of 201°–292°.

d. 4-Chloro-1-ethyl-1H-pyrazolo[3,4-b]pyridine-5-carbonyl chloride

A mixture of 31 g of 1-ethyl-4-hydroxy-1H-pyrazolo[3,4-b]pyridine-5-carboxylic acid (0.15 mOl) and 125 ml of thionylchloride is heated under reflux for 4 hours. Then the thionylchloride is evaporated completely in vacuo; the oily residue (33 g) which crystallizes quickly is used without purification for the next reaction step.

e. 4-Butylamino-1-ethyl-1H-pyrazolo[3,4-b]pyridine-5-N(N-butyl)carboxamide, hydrochloride To a solution of 24.4 g of 4-chloro-1-ethyl-1H-pyrazolo[3,4-b]pyridine-5-carbonylchloride (0.1 mol) in 75 ml of dry benzene, 32 g of n-butylamine (0.44 mol) dissolved in 75 ml of benzene is slowly added with cooling. The reaction mixture is allowed to remain at room temperature while stirring for 6 hours, during which time a precipitate forms. The mixture is evaporated to dryness in vacuo. The residue is washed with water, filtered under suction and dried in a desiccator over phosphorous pentoxide. 4-Butylamino-1-ethyl-1H-pyrazolo[3,4-b]pyridine-5-(N-butyl)carboxamide (26 g = 82%) is recrystallized from ligroin, and has a melting point of 98°–99°. The hydrochloride is formed by adding ethereal hydrogen chloride solution to a cooled solution of the carboxamide in ethylacetate. The precipitate is recrystallized from absolute alcohol, and has a melting point of 236°–237° decomp.

EXAMPLE 2

1-Ethyl-3-methyl-4-(1-piperidino)-1H-pyrazolo[3,4-b]pyridine-5-(N-piperidyl)-carboxamide a. [[(1-ethyl-3-methyl-5-pyrazolyl)amino]methylene]-malonic acid diethyl ester 12.5 g of 1-ethyl-3-methyl-5-aminopyrazole (0.1 mol) and 21.6 g of ethoxymethylene malonic acid diethyl ester (0.1 mol) are heated to 120° (bath temperature) for 2 hours with stirring. The ethanol formed by this reaction is removed by means of a water aspirator. Vacuum distillation (b.p. $_{0.05}$ 152°–153°) yields 24.0 g (81.5% of theory) of a quickly crystallizing oil, [[(1-ethyl-3-methyl-5-pyrazolyl)-amino]methylene]malonic acid diethyl ester, m.p. 60°–67°. The product, recrystallized from ligroin (90°–100°), melts at 69°–70°.

b. 1-ethyl-4-hydroxy-3-methyl-1H-pyrazolo[3,4-b]pyridine-5-carboxylic acid and ethyl ester 14.8 g of [[(1-ethyl-3-methyl-5-pyrazolyl)amino]methylene]malonic acid diethyl ester (0.05 mol) is dissolved in 50 g of diphenyl ether. The reaction mixture is heated to 235°–250° (bath temperature) and allowed to react at this temperature for 1 to 2 hours, while continuously distilling off the resulting ethanol. The last part of the alcohol is removed by means of a water aspirator. The diphenyl ether is separated by distillation with a fractionation column in vacuo. The 1-ethyl-4-hydroxy-3-methyl-1H-pyrazolo[3,4-b]pyridine-5-carboxylic acid ethyl ester is obtained at b.p.$_{0.1-0.5}$ 125°–129°, yield 10.7 g = 86% of theory, m.p. 91-93°. The compound is recrystallized from ligroin (90°–100°), and has a melting point of 93°–94°. Hydrolysis of this product with aqueous sodium hydroxide yields 1-ethyl-4-hydroxy-3-methyl-1H-pyrazolo[3,4-b]pyridine-5-carboxylic acid, m.p. 212°–213°.

c. 4-Chloro-1-ethyl-3-methyl-1H-pyrazolo[3,4-b]pyridine-5-carbonyl chloride 22 g of 1-ethyl-4-hydroxy-3-methyl-1H-pyrazolo[3,4-b]pyridine-5-carboxylic acid (0.1 mol) and 75 ml of thionyl chloride are refluxed for 4 hours. The clear thionyl chloride solution is evaporated to dryness in vacuo. The residue, weighing 24 g (93% of theory), contains the crude 4-chloro-1-ethyl-3-methyl-1H-pyazolo[3,4-b]pyridine-5-carbonyl chloride, which can be used without further purification for the next reaction step. A sample recrystallized from cyclohexane melts at 68°–70°.

d. 1-Ethyl-3-methyl-4-(1-piperidino)-1H-pyrazolo[3,4-b]pyridine-5-(N-piperidyl)-carboxamide To a solution of 7.7 g of 4-chloro-1-ethyl-3-methyl-1H-pyrazolo[3,4-b]pyridine-5-carbonyl chloride (0.03 mol) in 100 ml of dry benzene, 11.2 g of piperidine (0.144 mol) is added dropwise. The mixture is stirred at 50° (bath temperature) for 3 hours. After filtering the precipitated piperidine hydrochloride under suction the benzene filtrate is evaporated in vacuo, and the remaining oil is treated with water and then extracted with ether. The ethereal solution is dried over sodium sulfate and filtered. Addition of ethereal hydrogen chloride precipitates the hydrochloride of the 1-ethyl-3-methyl-4-(1-piperidino)-1H-pyrazolo[3,4-b]pyridine-5-(N-piperidyl)-carboxamide, which is filtered under suction and recrystallized from a mixture of ethyl acetate and absolute alcohol (1:1). Yield 9.2 g (78.6%), m.p. 197°–199° decomp.

EXAMPLE 3

4-Amino-1-ethyl-3-methyl-1H-pyrazolo[3,4-b]pyridine-5-(N-2,2-diethoxyethyl)-carboxamide a. 4-Chloro-1-ethyl-3-methyl-1H-pyrazolo[3,4-b]pyridine-5-(N-2,2-diethoxyethyl)carboxamide 15.5 g of 4-chloro-1-ethyl-3-methyl-1H-pyrazolo[3,4-b]pyridine-5-carbonyl chloride (0.06 mol) dissolved in 200 ml of dry ether is cooled to a temperature of −2°. By adding a solution of 16 g of aminoacetaldehyde-diethylacetal (0.12 mol) in 75 ml of dry ether dropwise to the reaction mixture while stirring, the internal temperature rises to 18° within 20 minutes. Stirring is continued for an additional 20 minutes at room temperature. The precipitate is filtered under suction, washed with ether and suspended in about 125 ml of water. After vigorous stirring, the crude product is again filtered under suction, washed with water and dried over phosphorous pentoxide in a desiccator. Yield 15.5 g (73%), m.p. 121°–123°. Recrystallization of the 4-chloro-1-ethyl-3-methyl-1H-pyrazolo[3,4-b]pyridine-5-(N-2,2-diethoxyethyl)carboxamide gives a compound with a melting point of 123°–125°. A further crop of 3 g is obtained by working up of the mother liquor.

b. 4-Amino-1-ethyl-3-methyl-1H-pyrazolo[3,4-b]pyridine-5-(N-2,2-diethoxyethyl)carboxamide 3.5 g of 4-chloro-1-ethyl-3-methyl-1H-pyrazolo[3,4-b]pyridine-5-(N-diethoxyethyl)carboxamide (0.01 mol) and 60 ml of alcoholic ammonia (about 65 g/l) are heated to 125°–130° (bath temperature) in an autoclave for 7 hours. Subsequently, the alcohol is removed in vacuo and the residue is treated with water, filtered under suction and dried over phosphorous pentoxide in a desiccator. 2.7 g (80.6%) of 4-amino-1-ethyl-3-methyl-1H-pyrazolo[3,4-b]pyridine-5-(N-2,2-diethoxyethyl)carboxamide are obtained, m.p. 151°–153°. Recrystallization from benzene lets the melting point rise to 155°–157°.

EXAMPLE 4

4-Butylamino-1-ethyl-1H-pyrazolo[3,4-b]pyridine-5-(N-pyrrolidyl)carboxamide, hydrochloride a. 4-chloro-1-ethyl-1H-pyrazolo[3,4-b]pyridine-5-carboxylic acid ethyl ester A mixture of 12 g of [[(1-ethyl-5-pyrazolyl)amino]-methylene]malonic acid diethyl ester (0.043 mol), obtained as in Example 1a, and 70 ml of phosphorus oxychloride are refluxed for 10 hours. The excess phosphorus oxychloride is removed in vacuo and the oily residue is treated with 50 ml of water which causes the oil to become crystalline. The solid material is filtered off under suction and dried in a desiccator; yield 8.5 g = 79% of theory. The 4-chloro-1-ethyl-1H-pyrazolo[3,4-b]pyridine-5-carboxylic acid ethyl ester is recrystallized from N-hexane, m.p. 62°.

b. 4-Butylamino-1-ethyl-1H-pyrazolo[3,4-b]pyridine-5-carboxylic acid ethyl ester To a solution of 5.08 g of 4-chloro-1-ethyl-1H-pyrazolo[3,4-b]pyridine-5-carboxylic acid ethyl ester (0.02 mol) in 20 ml of benzene is added 2.92 g of n-butylamine (0.04 mol). This mixture is kept at room temperature for 3 days. After this time, the separated butylamine hydrochloride is filtered under suction and the filtrate is evaporated in vacuo to dryness. The residue, 4-butylamino-1-ethyl-1H-pyrazolo[3,4-b]pyridine-5-carboxylic acid ethylester, is recrystallized from hexane, m.p. 82°–83°. The total yield amounts to 5.3 g = 91.5% of theory.

c. 4-Butylamino-1-ethyl-1H-pyrazolo[3,4-b]pyridine-5-carboxylic acid 29 g of 4-butylamino-1-ethyl-1H-pyrazolo[3,4-b]pyridine-5-carboxylic acid ethyl ester (0.1 mol) is hydrolized with 600 ml of aqueous sodium hydroxide (0.8 N) at 60°–70° (bath temperature) with stirring for 14 hours. After acidification with hydrogenchloride, 25.5 g of 4-butylamino-1-ethyl-1H-pyrazolo[3,4-b]pyridine-5 -carboxylic acid, m.p. 208°–210°, (yield 97%) are obtained. The compound is recrystallized from ethanol, and has a melting point of 213°–214°.

d. 4-Butylamino-1-ethyl-1H-pyrazolo[3,4-b]pyridine-5-carbonyl chloride 26.2 g of 4-butylamino-1-ethyl-1H-pyrazolo[3,4-b]pyridine-5-carboxylic acid (0.1 mol) and 100 ml of thionyl chloride are refluxed for 4 hours. The thionyl chloride is removed by means of a water aspirator. The residue, containing the crude 4-butylamino-1-ethyl-1H-pyrazolo[3,4-b]pyridine-5-carbonyl chloride, is recrystallized from benzene, and has a melting point of 142°–145°. Yield 23.5 g = 84% of theory.

e. 4-Butylamino-1-ethyl-1H-pyrazolo[3,4-b]pyridine-5-(N-pyrrolidyl)carboxamide, hydrochloride 22.4 g of 4-butylamino-1-ethyl-1H-pyrazolo[3,4-b]pyridine-5-carbonyl chloride (0.08 mol) is dissolved in 100 ml of dry chloroform. To the solution is added first 8.0 g of triethylamine and subsequently, while stirring, 12.5 g of pyrrolidine in 50 ml of chloroform drop by drop. Stirring is continued at room temperature for 2 hours. The reaction mixture is then evaporated in vacuo to dryness and the residue is treated with 150 ml of water. The remaining oil is extracted with 150 ml of ether, the ethereal solution is washed twice with water and then dried over sodium sulfate. Adding ethereal hydrogen chloride to the dried and filtered solution precipitates the 4-butylamino-1-ethyl-1H-pyrazolo[3,4-b]pyridine-5-(N-pyrrolidyl)-carboxamide, hydrochloride, which after filtering under suction is recrystallized from a mixture of ethyl acetate and absolute alcohol (6:1). Yield 19.7 g (70.3%), m.p. 170°–172°.

EXAMPLES 5–8

The following additional compounds are produced by the foregoing procedures having the following formula

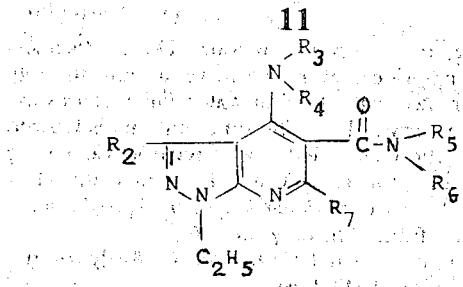

| Example | Procedure according to Example | $R_2$ | $R_3$ | $R_4$ | $R_5$ | $R_6$ | $R_7$ | m.p. °C |
|---|---|---|---|---|---|---|---|---|
| 5 | 2 | $CH_3$ | $-CH_2-CH_2-CH_2-CH_2-$ ($R_3$&$R_4$ form heterocyclic with N) | | $-CH_2-CH_2-CH_2-CH_2-$ ($R_5$&$R_6$ form heterocyclic with N) | | H | 116–117 |
| 6 | 4 | H | $CH_3-CH_2-CH_2-CH_2-$ | H | $-CH_2-CH_2-CH_2-CH_2-$ ($R_5$&$R_6$ form heterocyclic with N) | | H | Hydrochloride 149–152 dec. |
| 7 | 4 | H | $CH_3-CH_2-CH_2-CH_2-$ | H | $(OC_2H_5)_2CH-CH_2$ | | H | H | 117–119 |
| 8 | 4 | H | $CH_3-CH_2-CH_2-CH_2-$ | H | H | | H | H | 144–145 |

EXAMPLE 9

4-Butylamino-1H-pyrazolo[3,4-b]pyridine-5-N,N-diethyl-carboxamide a. [[[1-(2-furyl)methyl-5-pyrazolyl]amino]methylene]malonic acid diethyl ester 163 g of 1-(2-furyl)methyl-5-aminopyrazole (1 mol) and 216 g of ethoxymethylene malonic acid diethyl ester (1 mol) are heated to 130° (bath temperature) until the theoretical amount of alcohol is distilled off. The remaining oil, [[[1-(2-furyl)methyl-5-pyrazolyl]amino]methylene]malonic acid diethyl ester, is recrystallized from methanol, yield 280 g (84%), m.p. 84°–86°.

b. 4-Hydroxy-1-(2-furyl)methyl-1H-pyrazolo[3,4-b]pyridine-5-carboxylic acid ethyl ester 250 g of [[[1-(2-furyl)methyl-5-pyrazolyl]amino]methylene]malonic acid diethyl ester (0.75 mol) is dissolved in 1 liter of diphenyl ether and heated to 240° for 2 hours. The ethanol formed is continuously distilled off. The solvent is removed in vacuo. The 4-hydroxy-1-(2-furyl)methyl-1H-pyrazolo[3,4-b]pyridine-5-carboxylic acid ethyl ester remains and is recrystallized from methanol, yield 248 g (86%), m.p. 103°–106°.

c. 4-Ethoxy-1-(2-furyl)methyl-1H-pyrazolo[3,4-b]pyridine-5-carboxylic acid ethyl ester 300 g of 4-hydroxy-1-(2-furyl)methyl-1H-pyrazolo[3,4-b]pyridine-5-carboxylic acid ethyl ester (1.05 mol) is dissolved in 1 liter of dimethylformamide. 210 g of potassium carbonate (1.5 mol) and 233 g of ethyl iodide are added. The mixture is heated at 60° with continuous stirring for 10 hours. The excess potassium carbonate is filtered off. On addition of 500 ml of water, 4-ethoxy-1-(2-furyl)methyl-1H-pyrazolo[3,4-b]pyridine-5-carboxylic acid ethyl ester precipitates and is recrystallized from methanol, yield 280 g (85%), m.p. 93°–96°.

d. 4-Ethoxy-1H-pyrazolo[3,4-b]pyridine carboxylic acid ethyl ester 31.5 g of 4-ethoxy-1-(2-furyl)methyl-1H-pyrazolo[3,4-b]pyridine-5-carboxylic acid ethyl ester (0.1 mol) and 20 g of selenium dioxide (0.18 mol) are suspended in 100 ml diethyleneglycol dimethylether. The mixture is heated with stirring at 160° and a few drops of water are added. The temperature is held steady for 1.5 hours. After cooling, 100 ml of water is added and the mixture is neutralized with a dilute solution of aqueous ammonia. Yellow crystals are formed, which yield on recrystallization from methanol 15.8 g of 4-ethoxy-1H-pyrazolo[3,4-b]pyridine-5-carboxylic acid ethyl ester (67%), m.p. 180°.

e. 4-Butylamino-1H-pyrazolo[3,4-b]pyridine-5-carboxylic acid ethyl ester 2.35 g of 4-ethoxy-1H-pyrazolo[3,4-b]pyridine-5-carboxylic acid ethyl ester (0.01 mol) is treated with 2.2 g of butylamine (0.03 mol) at 90° for 1 hour. After this period the mixture is cooled, diluted with 20 ml of water and the white crystalline precipitate is filtered off. Recrystallization from diethyl ether yields 1.7 g of 4-butylamino-1H-pyrazolo[3,4-b]pyridine-5-carboxylic acid ethyl ester (72%), m.p. 181°.

f. 4-Butylamino-1H-pyrazolo[3,4-b]pyridine-5-carboxylic acid 2.6 g of 4-butylamino-1H-pyrazlo[3,4-b]pyridine-5-carboxylic acid ethyl ester (0.01 mol) is treated with 1.1 g of sodium hydroxide in 30 ml of ethanol for 20 hours at room temperature. The solvent is removed in vacuo and the residue is dissolved in 10 ml of water. On acidification with acetic acid 4-butylamino-1H-pyrazolo[3,4-b]pyridine-5-carboxylic acid solidifies and is filtered off. The product is purified by recrystallization from acetic acid, yield 1.9 g (82%), m.p. 225°.

g. 4-Butylamino-1H-pyrazolo[3,4-b]pyridine-5-N,N-diethylcarboxamide 2.3 g of 4-butylamino-1H-pyrazolo[3,4-b]pyridine-5-carboxylic acid (0.01 mol) is refluxed with 10 ml of thionyl chloride for 5 hours. After this time the excess of thionyl chloride is removed in vacuo, the residue dissolved in 20 ml of dry tetrahydrofuran, and 2 g of diethylamine is added under cooling. The mixture is allowed to stand for 24 hours, then the solvent is evaporated to dryness and 20 ml water is added to the residue. The crystalline 4-butylamino-1H-pyrazolo[3,4-b]pyridine-5-N,N-diethyl-carboxamide is filtered and recrystallized from acetic acid ethyl ester, yield 2.1 g (70%), m.p. 130°.

EXAMPLE 10

4-Butylamino-1H-pyrazolo[3,4-b]pyridine-5-N-butyl-carboxamide a. [[[1-(4-picolyl)-5-pyrazolyl]amino]methylene]malonic acid diethyl ester 174 g of 1-(4-picolyl)-5-aminopyrazole and 216 g of ethoxymethylene malonic acid diethyl ester are heated with stirring at 140°, until the theoretical amount of alcohol has distilled off. The reaction mixture crystallizes on cooling. Recrystallization from ethyl acetate yields 220 g of [[[1-(4-picolyl)-5-pyrazolyl]amino]methylene]malonic acid diethyl ester (65%), m.p. 95°-97°.

b. 4-Hydroxy-1-(4-picolyl)-1H-pyrazolo[3,4-b]pyridine-5-carboxylic acid ethyl ester 86 g of [[[1-(4-picolyl)-5-pyrazolyl]amino]methylene]malonic acid diethyl ester (0.25 mol) is heated at 240° for 15 minutes. The dark oil is cooled and 200 ml of methanol is added. 4-Hydroxy-1-(4-picolyl)-1H-pyrazolo[3,4-b]pyridine-5-carboxylic acid ethyl ester crystallizes on standing, yield 33g (44%), m.p. 140°.

c. 4-Hydroxy-1H-pyrazolo[3,4-b]pyridine-5-carboxylic acid ethyl ester 3 g of 4-hydroxy-1-(4-picolyl-1H-pyrazolo[3,4-b]pyridine-5-carboxylic acid ethyl ester (0.01 mol) is dissolved in 20 ml of acetic acid. 2.2 g of selenium dioxide (0.02 mol) and 2–3 drops of water are added. The mixture is refluxed for 30 minutes and then filtered off. 4-Hydroxy-1H-pyrazolo[3,4-b]pyridine-5-carboxylic acid ethyl ester precipitates on cooling. Recrystallization from acetic acid yields 1.8 g (87%), m.p. 275°.

d. 4-Ethoxy-1H-pyrazolo[3,4-b]pyridine-5-carboxylic acid ethyl ester 4.1 g of 4-hydroxy-1H-pyrazolo[3,4-b]pyridine-5-carboxylic acid ethyl ester (0.02 mol), 5.6 g of potassium carbonate (0.04 mol) and 3.5 g of ethyl iodide (0.022 mol) are heated in 30 ml of dimethylformamide with stirring for 10 hours at 60°. After this time, the excess potassium carbonate is filtered off and 30 ml of water is added. 4-Ethoxy-1H-pyrazolo[3,4-b]pyridine-5-carboxylic acid ethyl ester precipitates and is recrystallized from methanol, yield 2 g (42.5%), m.p. 180°.

e. 4-Butylamino-1H-pyrazolo[3,4-b]pyridine-5-carboxylic acid ethyl ester

4-Ethoxy-1H-pyrazolo[3,4-b]pyridine-5-carboxylic acid ethyl ester is treated with butylamine at 90° for 1 hour. After this period the mixture is cooled, diluted with water and the white crystalline precipitate is filtered off. Recrystallization from diethyl ether yields 4-butylamino-1H-pyrazolo[3,4-b]pyridine-5-carboxylic acid ethyl ester.

f. 4-Butylamino-1H-pyrazolo[3,4-b]pyridine-5-carboxylic acid

4-Butylamino-1H-pyrazolo[3,4-b]pyridine-5-carboxylic acid ethyl ester is treated with sodium hydroxide in ethanol for 20 hours at room temperature. The solvent is removed in vacuo and the residue is dissolved in water. On acidification with acetic acid, 4-butylamino-1H-pyrazolo[3,4-b]pyridine-5-caboxylic acid solidifies and is filtered off. The product is purified by recrystallization from acetic acid.

g. 4-Butylamino-1H-pyrazolo[3,4-b]pyridine-5-N-butyl-carboxamide 4.6 g 4-Butylamino-1H-pyrazolo]3,4-b]pyridine-5-carboxylic acid (0.02 mol) is refluxed with 20 ml thionyl chloride for 5 hours. The excess of thionyl chloride is removed in vauco and the residue is dissolved in 40 ml dry tetrahydrofuran. 3 g of n-butylamine is added drop by drop under cooling and the mixture is stirred at room temperature for 24 hours. Then the solvent is evaporated and 20 ml of water is added to the residue. The crystalline 4-butylamino-1H-pyrazolo[3,4-b]pyridine-5-N-butylcarboxamide is filtered off, and recrystallized from methyl alcohol. Yield 4.2 g (73%), m.p. 227°-228°.

EXAMPLES 11-41

The following additional compounds are produced by the foregoing procedures having the following formula:

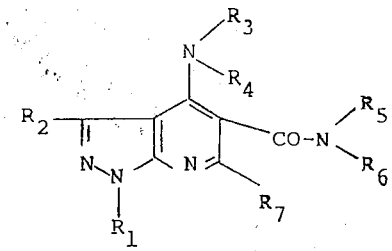

| Example | $R_1$ | $R_2$ | $R_3$ |
|---|---|---|---|
| 11 | H | H | $CH_3-CH_2-CH_2-CH_2-$ |
| 12 | H | H | $CH_3-CH_2-$ |
| 13 | H | $-CH_3$ | $-CH_2-CH_2-N(CH_3)-CH_2-CH_2-$ <br> ($R_3$ & $R_4$ form a heterocyclic with N) |
| 14 | $-CH_3$ | $-CH_3$ | $CH_3-CH_2-CH_2-CH_2-CH_2-$ |
| 15 | -⟨phenyl⟩ | $-CH_3$ | $-N=CH-CH=CH-$ <br> ($R_3$ & $R_4$ form a heterocyclic with N) |
| 16 | ⟨phenyl⟩$-CH_2-$ | H | $-CH_3$ |
| 17 | $CH_3-CH_2-CH_2-$ | $CH_3-CH_2-$ | $CH_3-CH_2-$ |
| 18 | $CH_3-CH_2-$ | H | $(CH_3)_2N-CH_2-CH_2-$ |
| 19 | $(CH_3)_2CH-$ | H | $-CH(CH_3)(C_2H_5)$ |
| 20 | $-C_2H_5$ | H | ⟨phenyl-$CF_3$⟩ |
| 21 | H | H | $-CH_2-CH_2-O-CH_2-CH_2-$ <br> ($R_3$ & $R_4$ form a heterocyclic with N) |
| 22 | H | H | $(CH_3)_2N-CH_2-CH_2-CH_2-$ |

-continued

| Example | $R_1$ | $R_2$ | $R_3$ |
|---|---|---|---|
| 23 | $-CH_2-CH-N(C_2H_5)_2$ | H | 2-chlorophenyl |
| 24 | tetrahydrothiopyranyl (S-containing 6-ring) | H | $-CH_2-CH_2-N(C_2H_5)-CH_2-CH_2-$ ($R_3$ & $R_4$ form a heterocyclic with N) |
| 25 | H | phenyl | $-C_2H_5$ |
| 26 | $-C_2H_5$ | H | $-CH_2CH=CH_2$ |
| 27 | H | H | $-C_2H_5$ |
| 28 | H | H | $CH_3CH_2\overset{\displaystyle \|}{\underset{\displaystyle O}{C}}-$ |
| 29 | $-C_2H_5$ | H | phenyl-C(=O)- |
| 30 | $-C_2H_5$ | H | 4-chlorophenyl-C(=O)- |
| 31 | $-C_2H_5$ | H | phenyl-$CH_2CH_2-$ |
| 32 | $-C_2H_5$ | H | phenyl-C-CH$_2$-CH$_2$C-$\overset{\|}{O}$ |
| 33 | $-C_2H_5$ | H | phenyl-$SO_2-$ |
| 34 | $-C_2H_5$ | H | $CH_3CH_2CH_2-SO_2-$ |
| 35 | $-C_2H_5$ | H | 3,4-dichlorophenyl |
| 36 | $-C_2H_5$ | H | phenyl-$CH_2(CH_2)_3CH_2-$ |
| 37 | $-C_2H_5$ | H | H |
| 38 | $-C_2H_5$ | H | $-C_4H_9$ |
| 39 | H | $-C_3H_7$ | $-C_4H_9$ |
| 40 | H | H | $-CH_2-CH_2-$ ($R_3$ & $R_4$ form a heterocyclic with N) |
| 41 | H | H | $-CH_2-CH_2-CH_2-$ ($R_3$ & $R_4$ form a heterocyclic with N) |

| Example | $R_4$ | $R_5$ | $R_6$ | $R_7$ |
|---|---|---|---|---|
| 11 | H | $CH_3-CH_2-$ | $CH_3-CH_2-$ | $-CH_3$ |
| 12 | H | $-CH_2-CH_2-N(CH_3)-CH_2-CH_2-$ ($R_5$ & $R_6$ form a heterocyclic with N) | | H |
| 13 | | $CH_3-CH_2-CH_2-$ | H | H |
| 14 | H | $-CH=N-CH=CH-$ ($R_5$ & $R_6$ form a heterocyclic with N) | | H |
| 15 | | $-CH_2-S-CH=CH-$ ($R_5$ & $R_6$ form a heterocyclic with N) | | $-CH_3$ |
| 16 | H | $-CH_2-N=CH-CH=CH-$ ($R_5$ & $R_6$ form a heterocyclic with N) | | H |
| 17 | $CH_3-CH_2-$ | $-CH_2-CH_2-CH_2-CH_2-CH_2-$ ($R_5$ & $R_6$ form a heterocyclic with N) | | $CH_3$ |
| 18 | H | $CH_3-CH_2-$ | $CH_3-CH_2-$ | H |

-continued

| Example | R₄ | R₅ | R₆ | R₇ |
|---|---|---|---|---|
| 19 | H |  (phenyl) | H | H |
| 20 | H | H | H | H |
| 21 | | —CH₃ | H | H |
| 22 | H | —CH(CH₃)₂ (—CH with two CH₃) | H | H |
| 23 | H | —CH₂—CH₂—CH₂—CH₂— (R₃&R₄ form a heterocyclic with N) | | H |
| 24 | | —CH₃ | —CH₂—CH₂—CH₂—CH₃ | H |
| 25 | H | —CH₃ | H | H |
| 26 | H | —C₂H₅ | —C₂H₅ | H |
| 27 | H | —C₂H₅ | H |  (phenyl) |
| 28 | H | CH₃—CH₂— | CH₃—CH₂— | H |
| 29 | H | —C₄H₉ | H | H |
| 30 | H | —C₄H₉ | H | H |
| 31 | H | —C₄H₉ | H | H |
| 32 | H | —C₄H₉ | H | H |
| 33 | H | —C₄H₉ | H | H |
| 34 | H | —C₄H₉ | H | H |
| 35 | H | —C₄H₉ | H | H |
| 36 | H | —C₄H₉ | H | H |
| 37 | H | CH₂CH₂—O—(CH₂)₂—CH₂— | H | H |
| 38 | H | (CH₃)₂N—CH₂—CH₂— | H | H |
| 39 | H | —C₄H₉ | H | H |
| 40 | H | —C₄H₉ | H | H |
| 41 | | —C₄H₉ | H | H |

What we claim is:
1. A compound of the formula

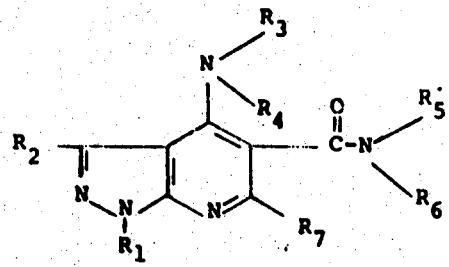

wherein R₁ is selected from the group consisting of hydrogen, lower alkyl, phenyl, phenyl-lower alkyl, and cycloalkyl having 3 to 7 carbon atoms;

R₂ is selected from the group consisting of hydrogen, lower alkyl, and phenyl;

the basic nitrogen group

is selected from the group consisting of
i. acyclic amino groups wherein R₃ and R₄ are each selected from the group consisting of hydrogen, lower alkyl, lower alkenyl, lower alkanoyl, phenyl, substituted phenyl, phenyl-lower alkyl, di-lower alkyl amino-lower alkyl, benzoyl, substituted benzoyl, phenyl-lower alkanoyl, substituted phenyl-lower alkanoyl, alkane sulfonyl, benzenesulfonyl, and substituted benzenesulfonyl and
ii. heterocyclic groups selected from the group consisting of pyrrolidino, piperidino and piperazino;

the basic nitrogen group

is selected from the group consisting of
i. acyclic amino groups wherein R₅ and R₆ are each selected from the group consisting of hydrogen, lower alkyl, alkoxy lower alkyl, dialkoxy lower alkyl, and di-lower alkylamino-lower alkyl and
ii. heterocyclic groups selected from the group consisting of pyrrolidino and piperidino;

R₇ is selected from the group consisting of hydrogen, lower alkyl, and phenyl;

with the proviso that at least one of the groups

and

is a heterocyclic group;
wherein lower alkyl and lower alkenyl refer to hydrocarbon groups having 1 to 8 carbon atoms;
wherein lower alkanoyl refers to acyl radicals of acids having the formula $C_nH_{2n+1}COOH$ wherein n must be 7 or less;
wherein substituted phenyl, substituted benzoyl, and substituted benzenesulfonyl refers to the respective moieties substituted with one or two substituents selected from the group consisting of lower alkyl, halogen, trifluoromethyl, amino, and carboxy;
and physiologically acceptable acid-addition salts thereof.

2. A compound as described in claim 1 wherein R₁, R₂, and R₇ are each selected from the group consisting of hydrogen and lower alkyl; R₃ and R₄ together with the nitrogen to which they are attached form a heterocyclic ring selected from the group consisting of pyrrolidino, piperidino, and piperazino; $R_5$ and $R_6$ together with the nitrogen to which they are attached form a heterocyclic ring selected from the group consisting of pyrrolidino and piperidino.

3. A compound as described in claim 1 wherein $R_1$, $R_2$, $R_6$, and $R_7$ are each selected from the group consisting of hydrogen and lower alkyl; $R_5$ is lower alkyl; $R_3$ and $R_4$ together with the nitrogen to which they are attached form a heterocyclic ring selected from the group consisting of pyrrolidino, piperidino, and piperazino.

4. A compound as described in claim 1 wherein $R_1$, $R_2$, and $R_7$ are each selected from the group consisting of hydrogen and lower alkyl; $R_3$ is lower alkyl; $R_4$ is hydrogen; $R_5$ and $R_6$ together with the nitrogen to which they are attached form a heterocyclic ring selected from the group consisting of pyrrolidino and piperidino.

5. A compound according to claim 1 wherein $R_1$ is ethyl; $R_2$ is methyl; $R_3$ and $R_4$ taken together with the nitrogen to which they are attached are piperidino; $R_5$ and $R_6$ taken together with the nitrogen to which they are attached are piperidino; and $R_7$ is hydrogen.

6. A compound according to claim 1 wherein $R_1$ is ethyl; $R_2$, $R_4$ and $R_7$ are hydrogen; $R_3$ is butyl and $R_5$ and $R_6$ taken together with the nitrogen to which they are attached are pyrrolidino.

7. A compound according to claim 1 wherein $R_1$ is ethyl; $R_2$ is methyl; $R_3$ and $R_4$ taken together with the nitrogen to which they are attached are pyrrolidino; $R_5$ and $R_6$ taken together with the nitrogen to which they are attached are pyrrolidino; and $R_7$ is hydrogen.

8. A compound according to claim 1 wherein $R_1$ is ethyl; $R_2$, $R_4$, and $R_7$ are hydrogen; $R_3$ is butyl; and $R_5$ and $R_6$ taken together with the nitrogen to which they are attached are pyrrolidino.

* * * * *

UNITED STATES PATENT AND TRADEMARK OFFICE
CERTIFICATE OF CORRECTION

PATENT NO. : 3,966,746
DATED : June 29, 1976
INVENTOR(S) : Hans Hoehn and Theodor Denzel It is certified that error appears in the above-identified patent and that said Letters Patent are hereby corrected as shown below:

Column 7, line 18, "byrazolyl" should read
-- pyrazolyl --.

Column 7, line 55, "1-ehyl" should read --1-ethyl--.

Column 7, line 59, "201°-292°" should read
-- 201°-202° --.

Column 8, line 2, "5-N(N-butyl)" should read
-- 5-(N-butyl) --.

Column 12, line 35, "1H-pyrazlo" should read
-- 1H-pyrazolo --.

Column 16, example 32, $R_3$ structure should read:

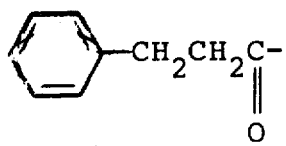

Signed and Sealed this

Ninth Day of November 1976

[SEAL]

Attest:

RUTH C. MASON
Attesting Officer

C. MARSHALL DANN
Commissioner of Patents and Trademarks